(12) United States Patent
Tanaka

(10) Patent No.: US 9,383,313 B2
(45) Date of Patent: Jul. 5, 2016

(54) TRANSMITTED LIGHT OBSERVATION APPARATUS

(71) Applicant: JIN CO., LTD., Gunma (JP)

(72) Inventor: Hitoshi Tanaka, Tokyo (JP)

(73) Assignee: JIN CO., LTD., Gunma (JP)

( * ) Notice: Subject to any disclaimer, the term of this patent is extended or adjusted under 35 U.S.C. 154(b) by 98 days.

(21) Appl. No.: 14/062,903

(22) Filed: Oct. 25, 2013

(65) Prior Publication Data

US 2014/0118744 A1    May 1, 2014

(30) Foreign Application Priority Data

Oct. 30, 2012  (JP) .................................. 2012-239561

(51) Int. Cl.
| | | |
|---|---|---|
| *G01N 21/00* | (2006.01) | |
| *G01N 21/59* | (2006.01) | |
| *G02C 7/10* | (2006.01) | |

(52) U.S. Cl.
CPC . *G01N 21/59* (2013.01); *G02C 7/10* (2013.01)

(58) Field of Classification Search
CPC ......... G01N 21/00; G01N 21/59; A61B 5/00; G02B 17/08; G02B 26/00; G02C 7/10
See application file for complete search history.

(56) References Cited

U.S. PATENT DOCUMENTS

| | | | | |
|---|---|---|---|---|
| 5,975,695 A | * | 11/1999 | Baiocchi et al. | ........... 351/159.6 |
| 6,084,662 A | * | 7/2000 | Seaburn | .......................... 356/73 |
| 2012/0206920 A1 | * | 8/2012 | Michelsen | ..................... 362/308 |
| 2013/0301051 A1 | * | 11/2013 | Pogosyan | ............. G01J 1/0411 |
| | | | | 356/432 |
| 2013/0335671 A1 | * | 12/2013 | Fleck | .................. G02B 27/017 |
| | | | | 349/62 |
| 2014/0107496 A1 | * | 4/2014 | Hellstrom et al. | ............ 600/478 |

FOREIGN PATENT DOCUMENTS

JP    2010-102278 A    5/2010

* cited by examiner

*Primary Examiner* — Tarifur Chowdhury
*Assistant Examiner* — Jamil Ahmed

(57) ABSTRACT

In order to allow for easy judgment of performance of optical material having a prescribed function, provided is a transmitted light observation apparatus comprising a light emitting section that generates light including light of a prescribed wavelength; a holding section that holds a first test material and a second test material arranged respectively in optical paths of the light generated by the light emitting section; and a reflecting portion that reflects at least a portion of the light transmitted respectively through the first test material and the second test material. Transmittance of the first test material for the light of the prescribed wavelength is different from transmittance of the second test material for the light of the prescribed wavelength. The light of the prescribed wavelength has a wavelength from 380 nm to 500 nm.

17 Claims, 6 Drawing Sheets

US 9,383,313 B2

TRANSMITTED LIGHT OBSERVATION APPARATUS

The contents of the following Japanese patent application are incorporated herein by reference:
No. 2012-239561 filed on Oct. 30, 2012.

BACKGROUND

1. Technical Field

The present invention relates to a transmitted light observation apparatus.

2. Related Art

Lenses have been proposed that use material processed to enable absorption of light having a particular wavelength, such as shown in Patent Document 1, for example. In addition, methods have been proposed for displaying, in a sales space, demonstration lenses that have been colored or decorated with a pattern or uniform design, and promoting sales of the lenses by attracting the customers to the decorations of the demonstration lenses, such as shown in Patent Document 2, for example.

Patent Document 1: U.S. Pat. No. 5,975,695
Patent Document 2: Japanese Patent Application Publication No. 2010-102278

However, with the method described in Patent Document 2, it is impossible to observe the light that has transmitted through the optical material. Therefore, customers cannot easily judge the performance of the optical material that provides a certain function.

SUMMARY

Therefore, it is an object of an aspect of the innovations herein to provide a transmitted light observation apparatus, which is capable of overcoming the above drawbacks accompanying the related art. The above and other objects can be achieved by combinations described in the claims. According to a first aspect of the present invention, provided is a transmitted light observation apparatus comprising a light emitting section that generates light including light of a prescribed wavelength; a holding section that holds a first test material and a second test material arranged respectively in optical paths of the light generated by the light emitting section; and a reflecting portion that reflects at least a portion of the light transmitted respectively through the first test material and the second test material. Transmittance of the first test material for the light of the prescribed wavelength is different from transmittance of the second test material for the light of the prescribed wavelength.

In the transmitted light observation apparatus, the light of the prescribed wavelength may have a wavelength from 380 nm to 500 nm. The reflecting portion may include a light path visibility section that is arranged in the optical paths of the light transmitted respectively through the first test material and the second test material and that causes the optical paths of the light transmitted respectively through the first test material and the second test material to become visible. The light path visibility section may include a transparent material that is transparent with respect to visible light. The transparent material may include therein a light scattering section that scatters the light of the prescribed wavelength.

In the transmitted light observation apparatus, the light emitting section may include a first light source that radiates the light including the light of the prescribed wavelength toward the first test material, and a second light source that radiates the light including the light of the prescribed wavelength toward the second test material. The transmitted light observation apparatus may further comprise the first test material and the second test material. The first test material and the second test material may be optical components for use in eyewear.

The summary clause does not necessarily describe all necessary features of the embodiments of the present invention. The present invention may also be a sub-combination of the features described above.

DESCRIPTION OF EXEMPLARY EMBODIMENTS

Hereinafter, some embodiments of the present invention will be described. The embodiments do not limit the invention according to the claims, and all the combinations of the features described in the embodiments are not necessarily essential to means provided by aspects of the invention.

Figure 1:
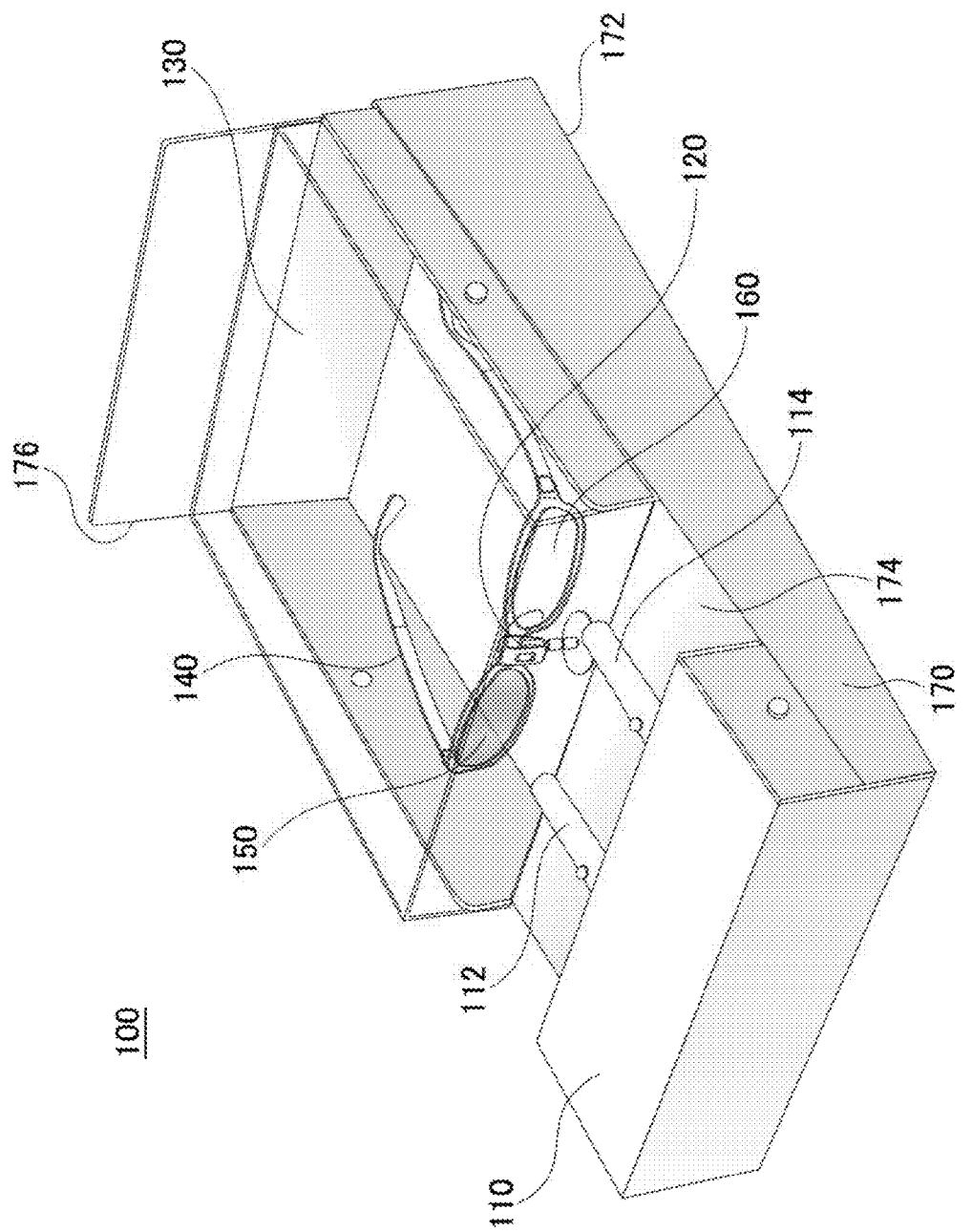
FIG. 1 is a perspective view of a transmitted light observation apparatus 100 according to a first embodiment of the present invention.
Figure 2:
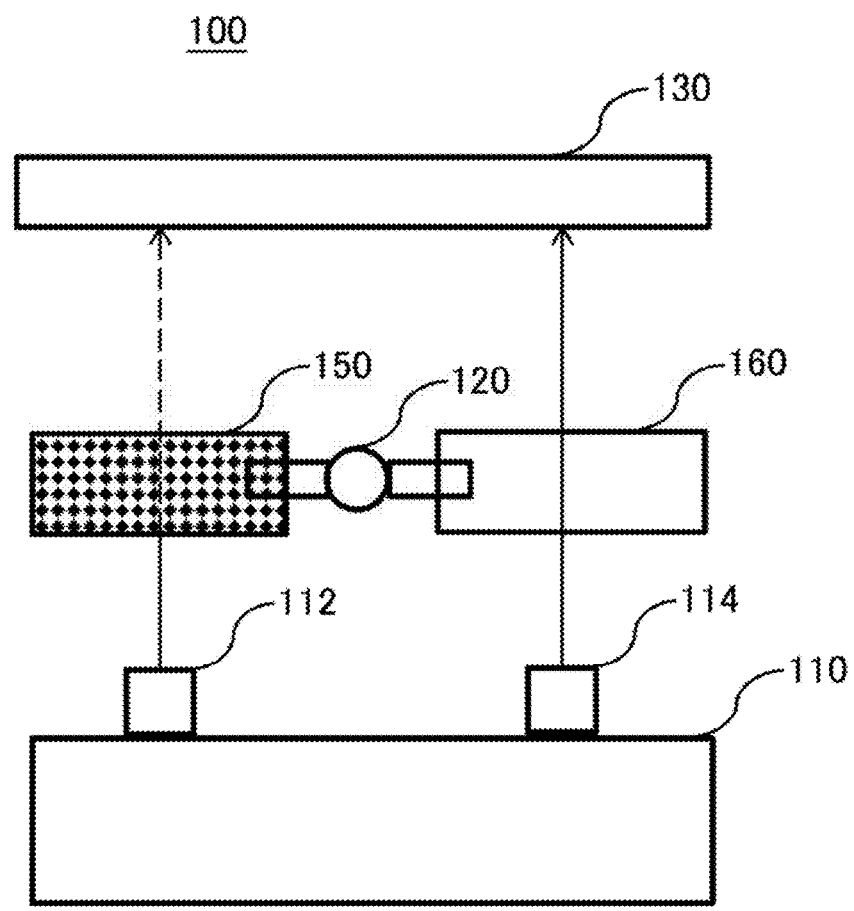
FIG. 2 is a schematic view of the transmitted light observation apparatus 100 according to the first embodiment as seen from above.

FIG. 1 is a perspective view of a transmitted light observation apparatus 100 according to a first embodiment of the present invention. FIG. 2 is a schematic view of the transmitted light observation apparatus 100 as seen from above. The transmitted light observation apparatus 100 includes a light emitting section 110, a holding section 120, and a reflecting portion 130. A first test material 150 and a second test material 160 are held by the holding section 120 between the light emitting section 110 and the reflecting portion 130. The first test material 150 and the second test material 160 have different transmittances for a prescribed wavelength of light.

The light emitting section 110 generates light including light of the prescribed wavelength. The light emitting section 110 may include a first light source 112 that radiates the light including the light of the prescribed wavelength toward the first test material 150, and a second light source 114 that radiates the light including the light of the prescribed wavelength toward the second test material 160. The first light source 112 and the second light source 114 may emit laser light or coherent light. The first light source 112 and the second light source 114 may be LED light sources.

The light of the prescribed wavelength radiated by the first light source 112 and the second light source 114 may have a wavelength of 380 nm to 500 nm. Most preferably, the light of the prescribed wavelength is blue light with a wavelength of 380 nm to 495 nm. The first light source 112 and the second light source 114 may generate light having substantially the same wavelength distribution and intensity. Here, "having substantially the same wavelength distribution and intensity"

means that when a normal observer perceives the two lights with their eyes, the observer cannot clearly recognize a difference between the lights.

The first test material 150 may be manufactured using a material that has been processed in a manner to decrease the transmittance of the light having the prescribed wavelength, e.g. blue light. For example, the first test material 150 may be manufactured using a material that absorbs the light of the prescribed wavelength and transmits other light in the visible wavelength range. The first test material 150 may be manufactured by forming a coating that absorbs or reflects the light of the prescribed wavelength, on the surface of glass or transparent plastic. Examples of the transparent plastic that can be used include cellulose triacetate (TAC), polycarbonate (PC), and norbornene-type polymers.

The transmittance of the first test material 150 for light having a wavelength in a first range may be less than the transmittance of the first test material 150 for light having a wavelength in a second range. The first wavelength range may be selected within a range from 380 nm to 500 nm, and the second wavelength range may be selected within a range from 500 nm to 750 nm. In other words, the transmittion rate of the first test material 150 for blue light may be less than the transmittance of the first test material 150 for other visible light.

The transmittance of the first test material 150 for blue light may be 90% or less, preferably no less than 30% and no greater than 85%, more preferably no less than 35% and no greater than 80%, and most preferably no less than 40% and no greater than 75%. The transmittance of the first test material 150 for all other visible light may be 80% or more, preferably no less than 85%, more preferably no less than 90%, and most preferably no less than 95%.

The transmittance of the second test material 160 for the light having the wavelength that the first test material 150 is processed to have a reduced transmittance for is greater than the transmittance of the first test material 150 for this light. The material that can be used for the second test material 160 includes glass, resin, and the like that is used for manufacturing common glasses. The second test material 160 need not undergo the processing that is applied to the first test material 150.

The second test material 160 may include an opening. If the second test material 160 includes an opening, the holding section 120 may hold a peripheral portion of the opening of the second test material 160, such that the opening of the second test material 160 is arranged in the path of the light. When the opening of the second test material 160 is arranged in the light path, the light of the prescribed wavelength passes through an atmosphere of air or the like, but passing through an atmosphere such as air may also be considered as passing through the second test material 160. The second test material 160 may be portion of an eyewear frame.

The first test material 150 and the second test material 160 may be optical components used in eyewear. The first test material 150 and the second test material 160 may be provided in the form of lenses for glasses supported on an eyewear frame 140, such as shown in FIG. 1. In the perspective view of FIG. 2, the frame 140 is omitted from the view.

The holding section 120 holds the first test material 150 and the second test material 160, such that the first test material 150 is arranged in the optical path of the light radiated from the first light source 112 and the second test material 160 is arranged in the optical path of the light radiated from the second light source 114. The holding section 120 may hold the first test material 150 and the second test material 160 either indirectly or directly. If the first test material 150 and the second test material 160 are lenses of glasses, the holding section 120 may hold the first test material 150 and the second test material 160 such that the centers of the lenses are arranged in the respective optical paths.

As shown in FIG. 1, the holding section 120 may indirectly hold the first test material 150 and the second test material 160 by supporting the bridge of the eyewear frame 140. The frame 140 may support the first test material 150 within the right-eye rim and support the second test material 160 within the left-eye rim.

The first test material 150 and the second test material 160 may be provided as glasses lenses that are only supported by other components, such as eyewear, or may be provided as flat plates or the like that differ from glasses lenses. The first test material 150 and the second test material 160 may be formed integrally.

If the first test material 150 and the second test material 160 are provided in a manner that is not supported by another member, such as eyewear, the holding section 120 may directly hold the first test material 150 and the second test material 160. If the first test material 150 and the second test material 160 are provided at a distance from each other instead of being formed integrally, the holding section 120 may include at least two components including a component for holding the first test material 150 and a component for holding the second test material 160.

The reflecting portion 130 reflects at least a portion of the light radiated from the first light source 112 and transmitted through the first test material 150 and the light emitted from the second light source 114 and transmitted through the second test material 160. If the transmittance of the first test material 150 for the light of the prescribed wavelength is less than the transmittance of the second test material 160 for the light of the prescribed wavelength, the reflecting portion 130 reflects the reflected light to be dark and shaped as a small circle or ellipse at the edge of a position corresponding to the optical path of the light radiated by the first light source 112. On the other hand, the reflecting portion 130 reflects the reflected light to be bright and shaped as a large circle at the edge of a position corresponding to the optical path of the light radiated by the second light source 114.

In this way, the light passing respectively through the first test material 150 and the second test material 160 can be made visible. As a result, an observer can easily judge the difference in optical performance between the first test material 150 and the second test material 160. The optical performance can be exemplified by the transmittance for the prescribed light.

The reflecting portion 130 may absorb a portion of the light having the prescribed wavelength. By absorbing a portion of the light having the prescribed wavelength, the reflecting portion 130 can prevent the light radiated by the first light source 112 and the second light source 114 from directly irradiating the eyes of the observer. For example, a component that absorbs a portion of the light having the prescribed wavelength may be arranged at least at a position on the reflecting portion 130 facing the light emitting section 110. The component absorbing a portion of the light having the prescribed wavelength may be paper, cloth, or the like. The reflecting portion 130 may be formed of a plastic material with satin cloth attached to the surface thereof.

The reflecting portion 130 may include a color conversion material that converts the color of light. The color conversion material may be material that absorbs blue light and emits light with a converted wavelength. The color conversion material may be a fluorescent material. The color conversion material may be arranged at least at a position facing the light emitting section 110. In this way, an observer can judge the optical performance of the first test material 150 and of the second test material 160, by observing the light with a wavelength differing from the light radiated by the first light source 112 and the second light source 114. Furthermore, by selecting a suitable color conversion material, the observer can clearly observe the difference in optical performance between the first test material 150 and the second test material 160.

The reflecting portion 130 may include a material that absorbs and is altered by the light having the prescribed wavelength. This material may be arranged at least at a position facing the light emitting section 110. In this way, the light passing respectively through the first test material 150 and the second test material 160 can be made visible. The reflecting portion 130 may include a component that diffuses the light of the prescribed wavelength. This material may be arranged at least at a position facing the light emitting section 110. In this way, an observer can more clearly observe the difference in optical performance between the first test material 150 and the second test material 160.

The reflecting portion 130 need not be arranged perpendicular to the optical path of the light radiated respectively by the first light source 112 and the second light source 114. Instead, the reflecting portion 130 may form an obtuse angle with respect to the optical paths of the light radiated respectively from the first light source 112 and the second light source 114. The region of the reflecting portion 130 irradiated by light changes according to the incident angle of the light irradiated from the first light source 112 and the second light source 114 with respect to the reflecting portion 130. Therefore, when the reflecting portion 130 is arranged to have an obtuse angle with respect to the optical path of the light radiated from the first light source 112 and the second light source 114, the region of the reflecting portion 130 irradiated by the light is larger than in a case where the reflecting portion 130 is perpendicular or at a sharp angle with respect to the light paths. As a result, the observer can more clearly observe the difference in optical performance between the first test material 150 and the second test material 160.

The transmitted light observation apparatus 100 may further have a configuration in which the first light source 112 and the first test material 150 move relative to each other, such that the first test material 150 can be removed from the optical path of the light generated by the first light source 112. For example, the light emitting section 110 may include a light source moving section that causes the first light source 112 to move, and the holding section 120 may hold a test material moving section that moves at least one of the first test material 150 and the second test material 160.

By moving the first light source 112 and the first test material 150 relative to each other, the difference between the reflected light occurring when the first test material 150 is arranged in the optical path of the light generated by the first light source 112 and the reflected light occurring when the first test material 150 is removed from the optical path can be easily confirmed. The movement of the first light source 112 or the first test material 150 need only enable confirmation of the reflected light in a case where the first test material 150 is removed from the optical path of the light radiated from the first light source 112, and may be linear movement or movement caused by rotation. At least one of the first light source 112 and the first test material 150 may be combined with a drive mechanism such as a motor to move automatically, or may be combined with a lever or the like to move according to manual operation.

Figure 3:
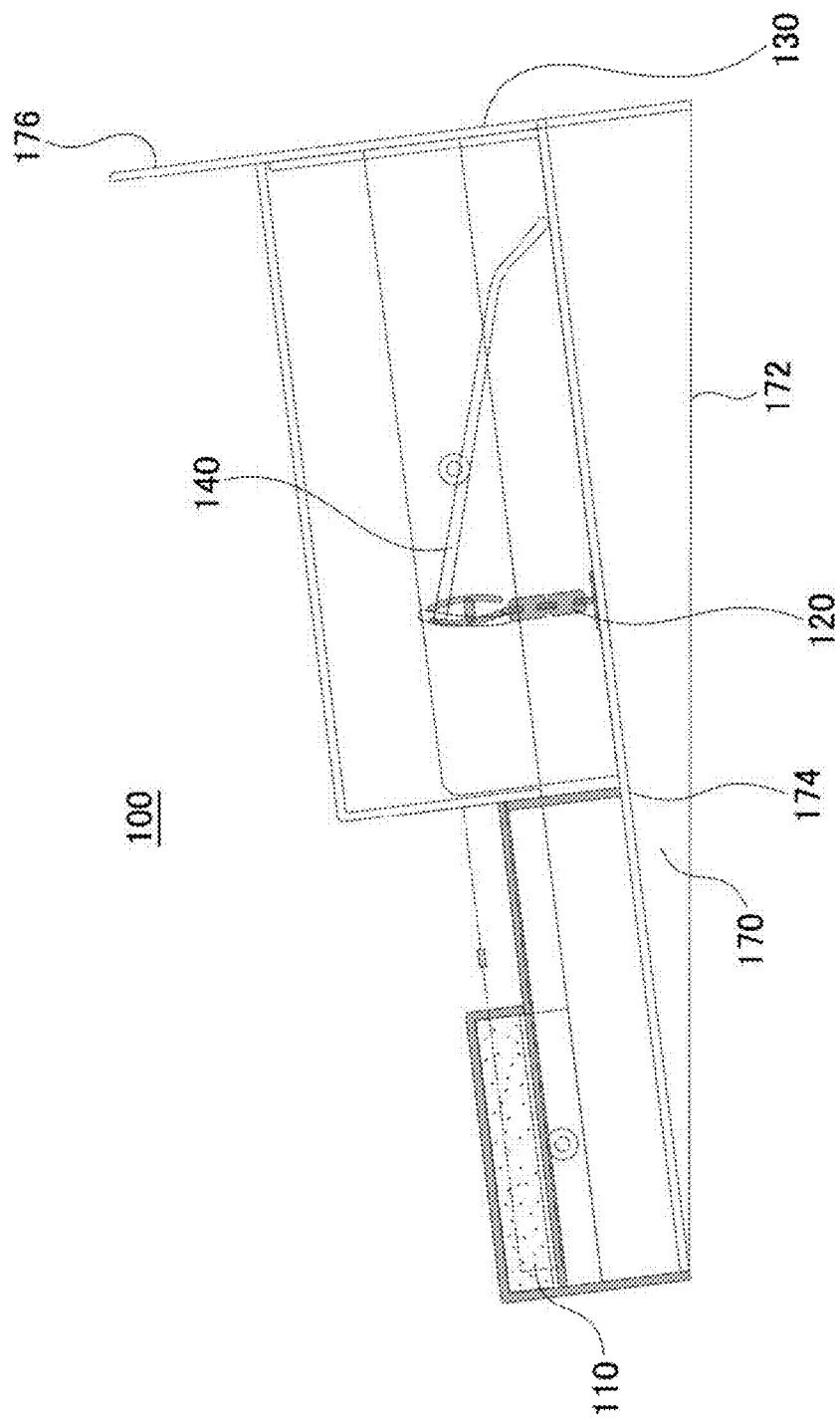
FIG. 3 is a side view of the transmitted light observation apparatus 100 according to the first embodiment.

FIG. 3 is a side view of the transmitted light observation apparatus 100. As shown in FIGS. 1 to 3 the transmitted light observation apparatus 100 may include a case 170 that houses each of the light emitting section 110, the holding section 120, and the reflecting portion 130.

The case 170 includes a bottom surface 172, a mounting surface 174, and a back surface 176. The mounting surface 174 may be at an angle relative to the bottom surface 172, such that the mounting surface 174 becomes farther from the bottom surface 172, in a direction from the light emitting section 110 towards the reflecting portion 130. The back surface 176 may be substantially perpendicular to the mounting surface 174.

In this way, the transmitted light observation apparatus 100 can be arranged with the bottom surface 172 used as a bottom placement surface, or with the back surface 176 used as a bottom placement surface. When the bottom surface 172 is used as the bottom placement surface, the transmitted light observation apparatus 100 can be placed more stably than when the back surface 176 is used as the bottom placement surface. When the back surface 176 is used as the bottom placement surface, the transmitted light observation apparatus 100 can be used in a narrower space than when the bottom surface 172 is used as the bottom placement surface.

In each of FIGS. 1 to 3, the transmitted light observation apparatus 100 is shown from above using the bottom surface 172 as the placement surface, the first light source 112 and second light source 114 are lined up with each other, and the first test material 150 and the second test material 160 are lined up with each other. However, when the bottom surface 172 is used as the placement surface, the first light source 112 and the second light source 114 may be lined up vertically, and the first test material 150 and the second test material 160 may also be lined up vertically.

Figure 4:
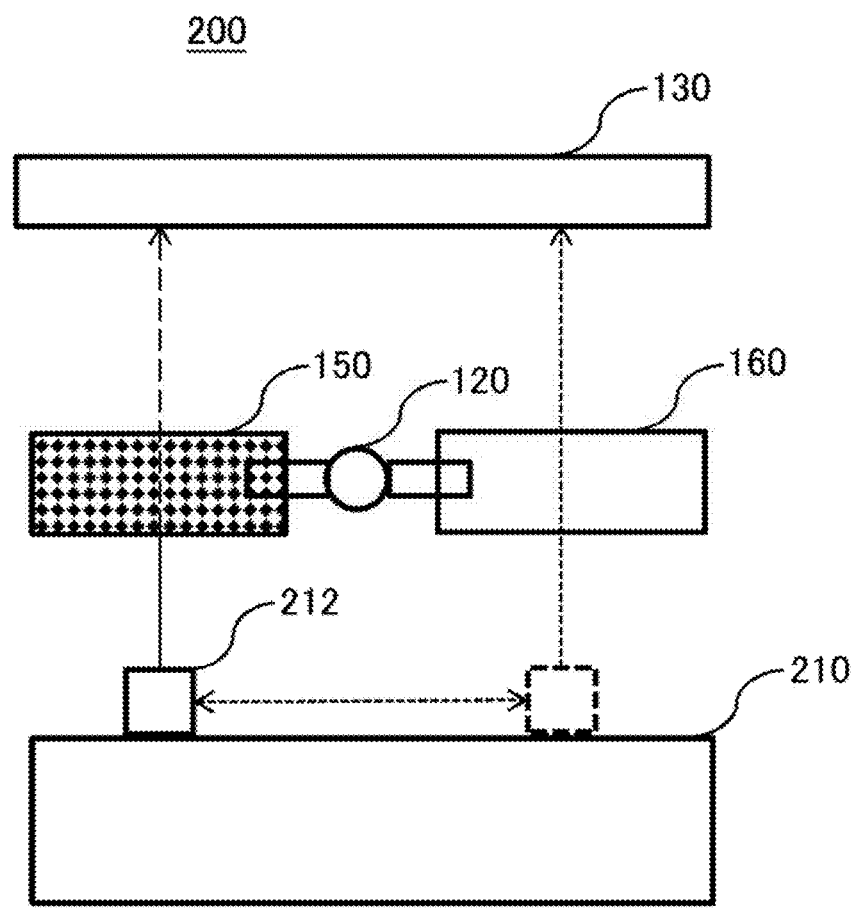
FIG. 4 is a schematic view of the transmitted light observation apparatus 200 according to the second embodiment as seen from above.

FIG. 4 is a schematic view of a transmitted light observation apparatus 200 according to a second embodiment of the present invention, as seen from above. The transmitted light observation apparatus 200 differs from the transmitted light observation apparatus 100 by including a light emitting section 210 that has a single light source 212. The transmitted light observation apparatus 200 is configured such that the light source 212 moves relative to the first test material 150 and the second test material 160 within a plane that is substantially parallel to the back surface of the transmitted light observation apparatus, thereby enabling light to be radiated to both the first test material 150 and the second test material 160 using the single light source 212. Aside from this point, the components of the transmitted light observation apparatus 200 may be configured in the same manner as those of the transmitted light observation apparatus 100.

The light source 212 may move linearly, such that light can be radiated from at least two points. A first position may be a position at which the light including light of the prescribed wavelength can be radiated toward the first test material 150, and a second position may be a position at which the light including light of the prescribed wavelength can be radiated toward the second test material 160.

The light source 212 may continuously radiate the light including light of the prescribed wavelength, even when moving between the first position and the second position. By continuously radiating the light including light of the prescribed wavelength, it becomes easier to recognize that there is less transmitted light when the light passes through the first test material 150 than when the light does not pass through the first test material 150. When the light source 212 is moved, the holding section 120 need not move, and may remain fixed.

Figure 5:
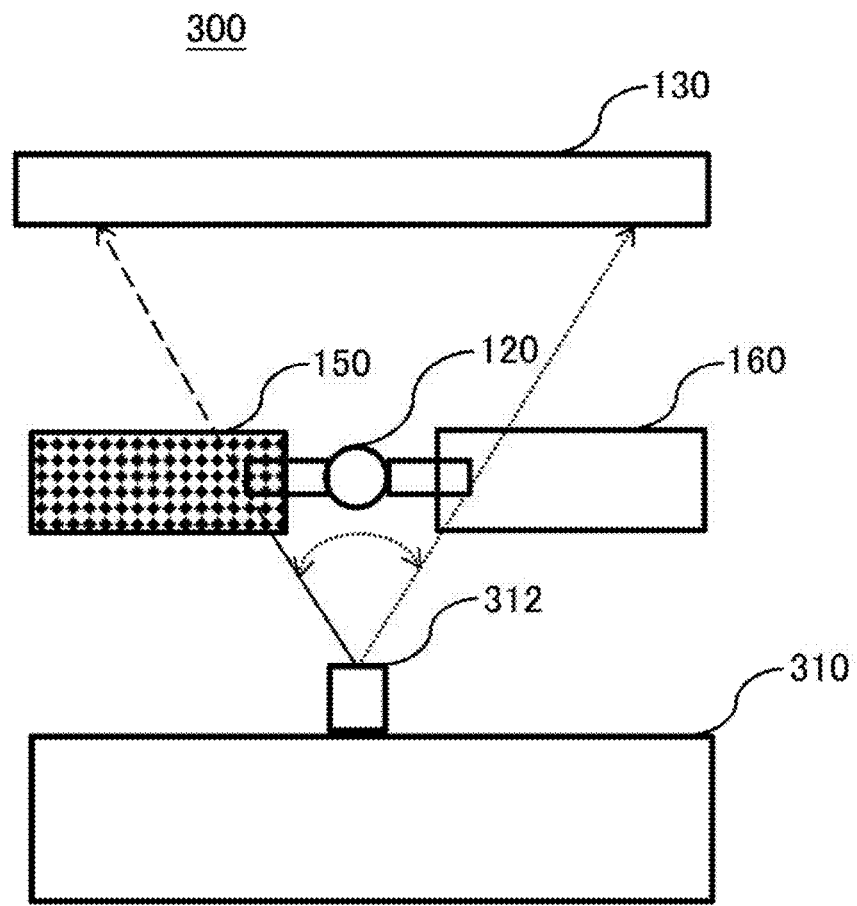
FIG. 5 is a schematic view of the transmitted light observation apparatus 300 according to the third embodiment as seen from above.

FIG. 5 is a schematic view of a transmitted light observation apparatus 300 according to a third embodiment of the present invention, as seen from above. The transmitted light observation apparatus 300 differs from the transmitted light observation apparatus 100 by including a light emitting section 310 that has a single light source 312. The transmitted light observation apparatus 300 differs from the transmitted light observation apparatus 200 in that the light source 312 moves rotationally relative to at least one of the first test material 150 and the second test material 160, thereby enabling light to be radiated to both the first test material 150 and the second test material 160 using the single light source 312. Aside from these points, the components of the transmitted light observation apparatus 300 may be configured in the same manner as those of the transmitted light observation apparatus 100 or transmitted light observation apparatus 200.

The light source 312 may be configured to radiate light from one end thereof facing the reflecting portion 130 while the other end is fixed, and to rotate the one end thereof with the other end thereof serving as the center. The light source 312 may move rotationally to enable the radiation of light from at least two positions. A first position may be a position at which the light including light of the prescribed wavelength can be radiated toward the first test material 150, and a second position may be a position at which the light including light of the prescribed wavelength can be radiated toward the second test material 160.

The light source 312 may continuously radiate the light including light of the prescribed wavelength, even when the one end is moving between the first position and the second position. By continuously radiating the light including light of the prescribed wavelength, it becomes easier to recognize that there is less transmitted light when the light passes through the first test material 150 than when the light does not pass through the first test material 150.

In both the second embodiment and the third embodiment, it is only necessary that the single light source or the first test material 150 and second test material 160 move, such that the single light source can irradiate both the first test material 150 and the second test material 160. For example, even if the single light source is fixed, the first test material 150 and the second test material 160 can be moved by moving the holding section. Furthermore, the single light source may continuously radiate the light including light of the prescribed wavelength, even when the holding section is moving. At least one of the single light source and the holding section may be combined with a drive mechanism such as a motor to move automatically, or may be combined with a lever or the like to be moved by a manual operation.

Figure 6:
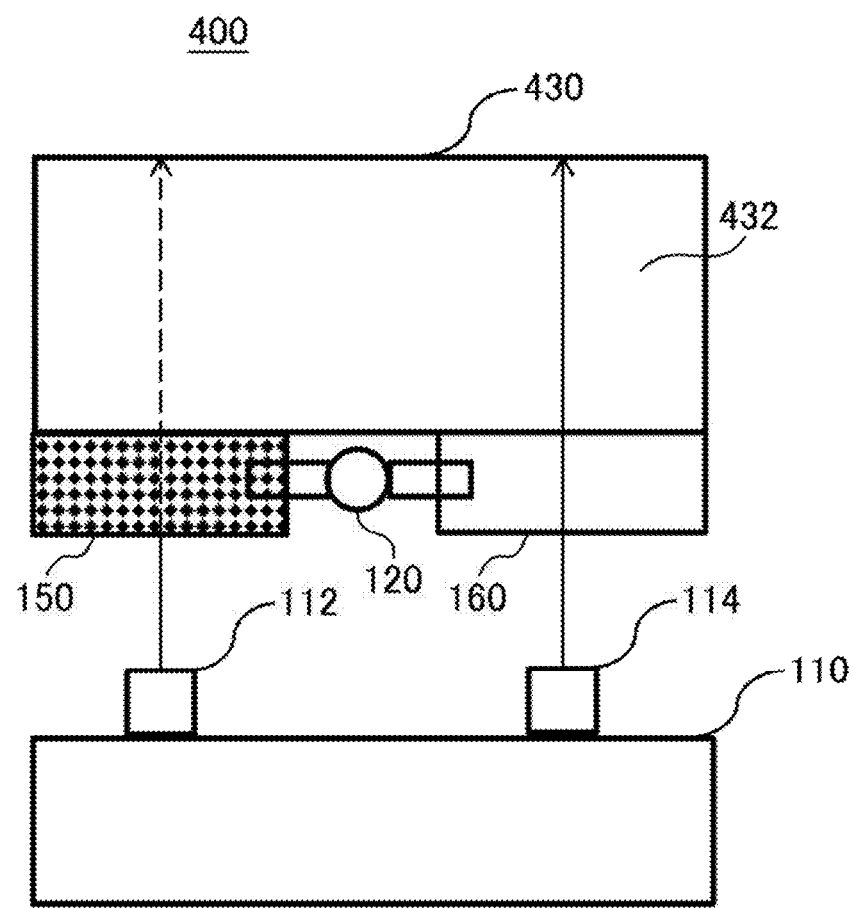
FIG. 6 is a schematic view of the transmitted light observation apparatus 400 according to the fourth embodiment as seen from above.

FIG. 6 is a schematic view of a transmitted light observation apparatus 400 according to a fourth embodiment of the present invention, as seen from above. The transmitted light observation apparatus 400 differs from the transmitted light observation apparatus 100, the transmitted light observation apparatus 200, and the transmitted light observation apparatus 300 by including a reflecting portion 430 that has a light path visibility section 432. Aside from this point, the components of the transmitted light observation apparatus 400 may be configured in the same manner as those of the transmitted light observation apparatus 100, transmitted light observation apparatus 200, or transmitted light observation apparatus 300.

The light path visibility section 432 includes a transparent material. The transparent material is transparent with respect to visible light, and includes a light scattering portion that diffuses the light of the prescribed wavelength. The light scattering portion is dispersed within the transparent material. Accordingly, when the light including the light of the prescribed wavelength is not being radiated, the light path visibility section 432 appears as a transparent component. The light scattering portion may include a color conversion material for converting the color of light. The color conversion material may absorb blue light and emit light with a converted wavelength. The color conversion material may be fluorescent material.

The light path visibility section 432 may be arranged behind the first test material 150 and the second test material 160 in the light progression direction. The transparent material included in the light path visibility section 432 includes the light scattering portion that scatters the light of the prescribed wavelength, and therefore the path of the light of the prescribed wavelength passing through the first test material 150 and the second test material 160 becomes visible.

If the transmittance of the first test material 150 for light of the prescribed wavelength is less than the transmittance of the second test material 160 for the light of the prescribed wavelength, the path of the light transmitted through the second test material 160 through the light path visibility section 432 will be seen more clearly than the path of the light transmitted through the first test material 150. In this way, the observer can easily judge the difference in optical performance between the first test material 150 and the second test material 160.

Blue light has a quality of being more easily scattered than other visible light. Accordingly, when the light of the prescribed wavelength is blue light, the path of the light having the prescribed wavelength in the light path visibility section 432 can be recognized by preparing a transparent material that has micro-particles added thereto as the light scattering section.

The transparent material may be a solid, liquid, or gas. The transparent material may be a gel. The transparent material need not be completely transparent. Vaporized dry ice may be used as a transparent material gas. Water or oil having micro-particles added thereto may be used as a transparent material liquid. If a gas or liquid is used as the transparent material, the light path visibility section 432 may be a container into which the gas or liquid is introduced as the transparent material.

A resin with micro-particles diffused therein or glass or aerogel with micro-particles diffused therein may be used as a transparent material solid. When a solid is used as the transparent material, the light path visibility section 432 and the transparent material may be formed as a single body. Furthermore, the light scattering section may be realized by forming fine cuts within the transparent material, instead of by adding micro-particles.

The light path visibility section 432 may include a light absorbing member that absorbs at least a portion of the light transmitted through the light path visibility section 432, on a surface thereof opposite the surface facing the light emitting section 110. This absorbing member may be paper or cloth, for example. The scattered reflection of light within the light path visibility section 432 can be prevented by absorbing a portion of the light having the scattered wavelength with the light absorbing member.

The fourth embodiment was described as having the light emitting section 110 such as included in the first embodiment, but the reflecting portion including the light path visibility section may be adopted in an embodiment in which the light emitting section has only one light source, such as in the second or third embodiments.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

What is claimed is:

1. A transmitted light observation apparatus comprising:
   a light source that generates first and second beams of light including light of a prescribed wavelength;
   a holder that holds a first test material and a second test material arranged respectively in optical paths of the first and second beams of light generated by the light source;
   a reflective surface that reflects at least a portion of the light transmitted respectively through the first test material and the second test material; and
   a transparent material that is arranged in the optical paths of the first and second beams of light transmitted respectively through the first test material and the second test material, the transparent material being transparent with respect to visible light and including a light scattering component, dispersed within the transparent material, that scatters the light of the prescribed wavelength so as to cause the optical paths of the first and second beams of light transmitted respectively through the first test material and the second test material to become visible as lines in the transparent material to an observer outside the first and second beams of light, wherein
   transmittance of the first test material for the light of the prescribed wavelength is different from transmittance of the second test material for the light of the prescribed wavelength.

2. The transmitted light observation apparatus according to claim 1, wherein
   the reflective surface reflects the at least a portion of the light transmitted respectively through the first test material and the second test material so as to make the light visible as an observable region on the reflective surface.

3. The transmitted light observation apparatus according to claim 2, wherein
   the observable region is a circle or an ellipse.

4. The transmitted light observation apparatus according to claim 2, wherein
   the reflective surface includes a color conversion material that converts the color of light.

5. The transmitted light observation apparatus according to claim 2, wherein
   the reflective surface includes a material that absorbs and is altered by light having a certain wavelength.

6. The transmitted light observation apparatus according to claim 1, wherein
   the light of the prescribed wavelength has a wavelength from 380 nm to 500 nm.

7. The transmitted light observation apparatus according to claim 1, wherein the light source includes:
   a first light source that radiates the first beam of light including the light of the prescribed wavelength toward the first test material; and
   a second light source that radiates the second beam of light including the light of the prescribed wavelength toward the second test material.

8. The transmitted light observation apparatus according to claim 1, further comprising the first test material and the second test material.

9. The transmitted light observation apparatus according to claim 1, wherein
   the first test material and the second test material are optical components for use in eyewear.

10. A transmitted light observation apparatus comprising:
    a light source that generates a beam of light including light of a prescribed wavelength;
    a holder that holds a first test material and a second test material arranged such that one of the first test material and the second test material is in the optical path of the beam of light generated by the light source; and
    a transparent material that is arranged in the optical path of the beam of light transmitted through the one of the first test material and the second test material, the transparent material being transparent with respect to visible light and including a light scattering portion, dispersed within the transparent material, that scatters the light of the prescribed wavelength so as to cause the beam of light transmitted through the one of the first test material and the second test material to become visible as a line in the transparent material to an observer outside the beam of light, wherein
    transmittance of the first test material for the light of the prescribed wavelength is different from transmittance of the second test material for the light of the prescribed wavelength, and
    the light source is movable between a first position at which the light is radiated toward the first test material and a second position at which the light is radiated toward the second test material.

11. The transmitted light observation apparatus according to claim 10, wherein the light source is movable linearly between the first position and the second position.

12. The transmitted light observation apparatus according to claim 10, wherein the light source is movable rotationally between the first position and the second position.

13. A transmitted light observation apparatus comprising:
    a light source that generates first and second beams of light including light of a prescribed wavelength;
    a holder that holds a first test material and a second test material arranged respectively in optical paths of the first and second beams of light generated by the light source; and
    a transparent material that is arranged in the optical paths of the first and second beams of light transmitted respectively through the first test material and the second test material, the transparent material being transparent with respect to visible light and including a light scattering component, dispersed within the transparent material, that scatters the light of the prescribed wavelength so as to cause the optical paths of the first and second beams of light transmitted respectively through the first test material and the second test material to become visible as lines in the transparent material to an observer outside the first and second beams of light, wherein
    transmittance of the first test material for the light of the prescribed wavelength is different from transmittance of the second test material for the light of the prescribed wavelength.

14. The transmitted light observation apparatus according to claim 13, wherein
    the light of the prescribed wavelength has a wavelength from 380 nm to 500 nm.

15. The transmitted light observation apparatus according to claim 13, wherein the light source includes:
   a first light source that radiates the first beam of light including the light of the prescribed wavelength toward the first test material; and
   a second light source that radiates the second beam of light including the light of the prescribed wavelength toward the second test material.

16. The transmitted light observation apparatus according to claim 13, further comprising the first test material and the second test material.

17. The transmitted light observation apparatus according to claim 13, wherein
   the first test material and the second test material are optical components for use in eyewear.

\* \* \* \* \*